United States Patent

Fancelli et al.

[11] Patent Number: 5,919,955
[45] Date of Patent: Jul. 6, 1999

[54] COMBINATORIAL SOLID PHASE SYNTHESIS OF A LIBRARY OF BENZOFURAN DERIVATIVES

[75] Inventors: Daniele Fancelli; Dino Severino, both of Milan; Maria Chiara Fagnola, Piacenza; Angelo Bedeschi, Milan, all of Italy

[73] Assignee: Pharmacia & Upjohn S.p.A., Milan, Italy

[21] Appl. No.: 08/981,478

[22] PCT Filed: May 13, 1997

[86] PCT No.: PCT/EP97/02601

§ 371 Date: Jan. 13, 1998

§ 102(e) Date: Jan. 13, 1998

[87] PCT Pub. No.: WO97/44338

PCT Pub. Date: Nov. 27, 1997

[30] Foreign Application Priority Data

May 23, 1996 [GB] United Kingdom .................... 9610813

[51] Int. Cl.⁶ .................................................. C07D 307/78

[52] U.S. Cl. ........................... 549/466; 549/470; 546/115; 546/116

[58] Field of Search ...................................... 546/115, 116; 549/466, 470

[56] References Cited

FOREIGN PATENT DOCUMENTS

WO 94/28028  12/1994  WIPO .

OTHER PUBLICATIONS

Arcadi et al Palladium Catalyzed Reaction of 2–Hydroxyaryl and Hydroxyheteroaryl Halides with 1–alkyner. Sep. 1986.

*Primary Examiner*—Amelia Owens
*Attorney, Agent, or Firm*—Oblon, Spivak, McClelland, Maier & Neustadt, P.C.

[57] ABSTRACT

The present invention relates to a process for the generation of a plurality of different benzofuran derivatives, and to the use of said benzofuran derivatives to search for novel classes of compounds and individual compounds possessing selected properties for pharmaceutical applications.

4 Claims, No Drawings

COMBINATORIAL SOLID PHASE SYNTHESIS OF A LIBRARY OF BENZOFURAN DERIVATIVES

The present invention relates to a process for the generation of a plurality (library) of different benzofuran derivatives, and to the use of said library to search for novel classes of compounds and individual compounds possessing selected properties for pharmaceutical applications.

Recently there has been an ever-increasing demand for chemical compounds that selectively act at specific biological recognition sites. These compounds can be used, inter alia, as inhibitors, activators or modulators of enzymes, as receptor ligands (agonists, antagonists or modulators), or for marking. To this purpose, methods have been developed to simultaneously synthesize a multiplicity (library) of different compounds and to assay them. These libraries (combinatorial compound libraries) usually consist of natural or modified aminoacids or nucleotides, and the like. The individual different ligands of these libraries are normally synthesized in parallel, either as mixtures or as physically separated individuals. These parallel syntheses make it possible to produce libraries containing a very large number of different ligands over a short period of time.

Also some libraries of small organic compounds have been synthesized, but the nature of the basic molecular backbone (scaffold) is mainly limited to aromatic and alicyclic compounds. Only some heterocyclic scaffolds have been synthesized. On the other hand, a large number of pharmacologically active compounds include heterocycles, and namely benzofused heterocyclic compounds. Therefore, there is still the need for new heterocyclic scaffolds to be synthesized and tested by means of combinatorial chemistry.

These libraries of small organic compounds are often synthesized on solid phase by using suitable resins and linkers. However, for this purpose a limited number of reactions is available, if compared with the number of organic reactions known in literature. Particularly, the use of organometallic catalysts in solid phase syntheses (SPS) is very limited, since many difficulties are encountered. For instance, the metal often separates at the reaction end contaminating the final products. Moreover, additives are usually added to the reaction medium which remain in suspension and contaminate the final products.

We have now surprisingly found that it is possible to synthesize in solid phase arrays of benzofuran derivatives of formula (I) as reported hereinbelow, by using organometallic catalysts. The use of solid phase synthesis allows purification of the final product from excess reagents and catalysts by simple washing. Moreover, it is possible to employ mild reaction conditions during the whole reaction, obtaining high yields and high purity degrees. It is to be noted that purity is very important in combinatorial chemistry, since the obtained arrays are usually tested as such, without any purification. Therefore, a low purity degree of the final products can be very harmful for biological testing. We have surprisingly found that the compound libraries generated by the instantly claimed process have a very high purity degree (typically, 85–95% by HPLC assay), which allows biological testing on the crude products with a high confidence degree, without any cross contaminations.

Therefore, a first object of the present invention is a process for preparing a plurality (library) of benzofuran derivatives of formula:

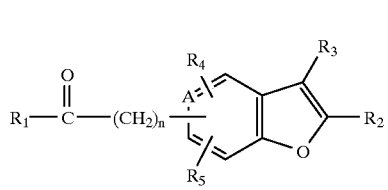

(I)

wherein:

$R_2$, $R_3$, $R_4$, and $R_5$ are, each independently, hydrogen or a structural diversity element, with the proviso that at least one of $R_2$, $R_3$, $R_4$, and $R_5$ is different from hydrogen;

$R_1$ is —$NR_6R_7$ or —$OR_8$, wherein $R_6$, $R_7$, and $R_8$ are, each independently, hydrogen or a structural diversity element;

A is CH or N, and may be in any of the unsubstituted positions of the phenyl ring; and n is zero or an integer from 1 to 4;

said process comprising the steps of:

(a) coupling to a solid support a first scaffold of formula:

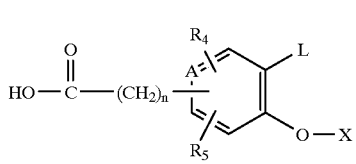

(II)

wherein:

$R_4$ and $R_5$ are, each independently, hydrogen or a structural diversity element;

A is CH or N, and may be in any of the unsubstituted positions of the phenyl ring;

n is zero or an integer from 1 to 4;

L is a leaving group; and

X is a hydroxy protecting group;

(b) deprotecting the hydroxyl group of the scaffold of formula (II) coupled to the solid support, to obtain a deprotected first scaffold of formula:

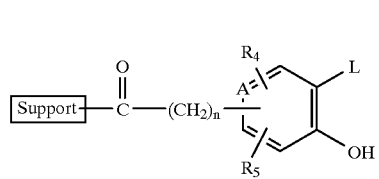

(IIa)

(c) reacting said deprotected first scaffold of formula (IIa) coupled to the solid support with a second scaffold of formula:

(III)

wherein $R_2$ and $R_3$ are, each independently, hydrogen or a structural diversity element;

in the presence of a transition metal as catalyst, preferably a Group VIII metal, more preferably Pd, in particular a Pd(0) complex or a Pd(II) salt, with or without a ligand to form an organometallic complex and optionally in the presence of a Cu(I) salt, to give the benzofuran derivatives of formula (Ia) supported on the solid support:

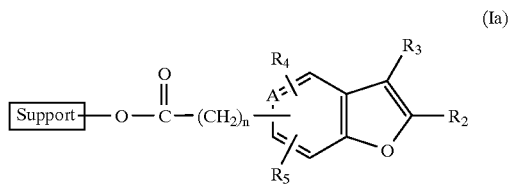

(Ia)

(d) optionally cleaving the compounds of formula (Ia) from the solid support to give the compounds of formula (I).

In formulas (II) and (IIa), the leaving group L may be, e.g., a halogen atom, preferably bromine or iodine, or a group —$OSO_2R_9$ in which $R_9$ is $C_1$–$C_6$ alkyl, $C_6$–$C_{10}$ aryl, $C_7$–$C_{12}$ arylalkyl or alkylaryl, optionally substituted by one or more fluorine atoms, preferably $R_9$ is —$CF_3$ or p-Me—$C_6H_4$—. The hydroxy blocking group X may be, e.g., an acyl group or a trisubstituted silyl group, preferably acetyl or t-butyldimethylsilyl.

In formulas (I), (Ia), (II), (IIa), and (III) with "structural diversity element" it is meant any moiety which can be systematically varied to produce combinatorial libraries of compounds based on the same structural nucleus. Any of a wide variety of structural diversity elements can be used. These elements would include any accessible combination of atoms selected from carbon, hydrogen, oxygen, sulphur, nitrogen, phosphorus, silicon, and halogen (fluorine, chlorine, bromine, iodine), typically organic radicals and optionally including also alkali, alkaline-earth or transition metals. Particularly, the structural diversity elements can be selected from straight or branched alkyl, cycloalkyl, aryl, arylalkyl, or alkylaryl, heterocyclyl, heterocyclylalkyl or alkylheterocyclyl, heteroaryl, heteroarylalkyl or alkylheteroaryl groups, or any combination thereof, optionally substituted with one or more functional groups such as: cyano, nitro, halogen, hydroxy, alkoxy, carbonyl, carboxyl, amide, optionally protected amino, ester, thioester, ether, thioether, halogen (fluorine, chlorine, bromine, iodine), sulfonyl, phosphate, and the like.

The alkyl group and alkyl moieties mentioned above may for instance be $C_1$–$C_6$ alkyl, typically $C_1$–$C_4$ alkyl, such as methyl, ethyl, i-propyl, n-propyl, t-butyl, s-butyl or n-butyl. The aryl moieties may be $C_6$–$C_{10}$ aryl, for instance phenyl or naphthyl. Alkoxy may be $C_1$–$C_6$ alkoxy, typically $C_1$–$C_4$ alkoxy, such as methoxy, ethoxy, i-propoxy, n-propoxy, t-butoxy, s-butoxy or n-butoxy.

Moreover, the structural diversity elements may be selected from: natural and/or synthetic amino acid residues or oligopeptides; nucleotide derivatives, and oligonucleotides constituted by natural and/or synthetic nucleotides; carbohydrates and carbohydrate derivatives, including oligosaccharides; naturally occurring or synthetic base structures of pharmaceutically active compounds including pharmacophores or metabolites thereof; natural or synthetic macromolecular structures, including also inorganic macromolecular products; and the like.

The process of the present invention is a "solid phase synthesis" (SPS), namely a reaction carried out on macroscopic particles, made of a material insoluble in the reaction medium, to which one of the reactants is bound in a sufficient amount. The reactants are usually linked by means of reactive groups on the surface of the support, e.g. amino, carboxyl, hydroxyl or halogen groups. These reactive groups are usually already constituents of the support, however they can also be applied or modified subsequently, before the reaction. For instance, the support can be modified by treating it with a cleavable linker, namely a molecule or group of molecules which can be bound at one side to the solid substrate and at the other side to the reacting molecules, forming a spacing between solid support and synthesized molecules, and which eventually can be readily removed. Acid-cleavable linkers are described e.g. by Atherton et al, *J. Chem. Soc. Perkin I* (1981), 538–546.

The resins customarily employed in SPS can be used in the present invention, e.g. commercially available resins which are usually employed in solid phase peptide synthesis or in combinatorial chemistry.

Each benzofuran derivative may be prepared in a quantity sufficient for screening purposes, and for analysis by conventional methods, such as HPLC and mass spectral analysis, to verify purity and integrity of the obtained compound.

Step (a)

Suitable reactions for step (a) include methods which are known in the art for covalently attaching organic molecules to solid supports, such as for instance the methods described by Fruchtel and Jung, *Angew. Chem. Int. Ed. Engl.* (1996) 35: 17–42, and by Thompson and Ellman, *Chem. Rev.* (1996), 555–600. Alternatively, the compounds of formula (II) may be covalently attached to the solid support according to the Mitsunobu reaction, described in *Synthesis* (1981) pag 1, or its modified versions.

Step (b)

The deprotection of the hydroxyl group may be performed according to known techniques usually employed to selectively removing hydroxyl protecting groups (see, e.g., Greene T. W. and Wuts P. G. M., "*Protective Groups in Organic Synthesis*", J. Wiley & Sons Ed., 1991).

Step (c)

A wide variety of reactants of formulas (II) and (III) are known and are usually readily available from commercial suppliers, or they may be prepared according to methods known in the art, such as those described e.g. in Houben-Weil, *Methoden der Organishen Chemie,* Vol. 5/2a.

The reaction between a compound of formula (IIa) and a compound of formula (III) may be usually performed in an organic solvent, in the presence of a base in excess. The reaction may be carried out at a temperature of from 40° to 120° C., preferably from 50° to 100° C., for a time ranging from a few hours to several days, and preferably from four hours to two days. When in the compounds of formula (III) $R_3$ is hydrogen, by using milder reaction conditions (lower temperatures and/or shorter times), intermediate products of formula:

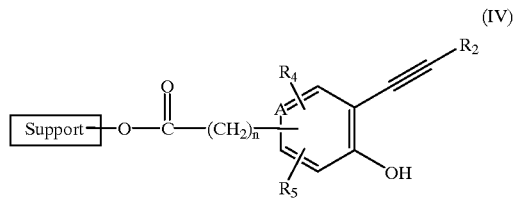

(IV)

may be obtained, which by simple heating can be converted into the compounds of formula (Ia) having $R_3$=H.

Suitable organic solvents for step (c) include, e.g., dimethylformamide (DMF), dioxane, tetrahydrofuran (THF), acetonitrile, dimethylsulfoxide, and acetone, or mixtures thereof. DMF, THF, dioxane, or mixtures thereof, are preferred. A suitable base may be, e.g., an organic base such as, mono- di- or tri-$C_1$–$C_4$-alkylamine, preferably triethylamine; a substituted $C_1$–$C_4$ alkyl guanidine, preferably tetramethylguanidine; 1,8-diazabicyclo-[5.4.0]-undec-7-ene (DBU), 1,5-diazabicyclo-[4,3,0]-non-5-ene (DBN), or 1,4-diazabicyclo-[2.2.2]-octane (DABCO), preferably DBU or DBN. Alternatively, an inorganic base may be used, such as an alkali metal or alkaline earth metal salt, e.g., $NaHCO_3$, $Na_2CO_3$, NaOAc, preferably $Na_2CO_3$, NaOAc.

The metal catalyst may be in the form of a salt or a complex with organic ligands. Particularly suitable metal catalyst are, for instance, the Group VIII metals, preferably Pd(0) complexes or a Pd(II) salt, with or without a ligand to form an organometallic complex. Preferred salts are halides and acetates, while the ligands may be selected from phosphorus-containing compounds, e.g. triphenylphosphine ($PPh_3$), tri(orto)tolylphosphine ($P(o-Tol)_3$), 1,2-bis (diphenyl-phosphino)ethane (dppe), or 1,1-bis (diphenylphosphino)-ferrocene (dppf).

The reaction may be optionally performed in the presence of Cu(I) salts, such as, e.g., a Cu(I) halide, $CU_2O$, CuCN, or a CuCN—LiCl complex, preferably CuI, CuCl, or $Cu_2O$.

Step (d)

A further element of variation may be introduced into the benzofuran structure depending on the reactants used for the cleavage. The cleavage from the solid support may be carried out with a suitable base, such as: an inorganic base, for instance an alkali metal or alkaline earth metal hydroxide or salt, e.g., $NaHCO_3$, $Na_2CO_3$, NaOH, $KHCO_3$, $K_2CO_3$, KOH, and LiOH, preferably $Na_2CO_3$, NaOH, KOH, $K_2CO_3$ or LiOH; a nitrogen-containing base, such as ammonia, mono- or di-$C_1$–$C_4$-alkylamine. In the former case, the process yields compounds of formula (I) having $R_1$ equal to —OH, whereas in the latter case compounds of formula (I) having $R_1$ equal to —$NR_6R_7$ are obtained. By treatment with a hydroalcoholic alkaline solution, compounds of formula (I) having $R_1$ equal to —$OR_8$ are obtained, wherein $R_8$ is different from hydrogen, possibly in admixture with the corresponding compounds having $R_1$ equal to —OH.

Operatively, the process object of the present invention can be carried out as follows. The resin bound substrate, prepared in a single batch as described above, is divided into equal portions in a 96-well Microtiter reaction plate. The above procedure may be performed by weighting a roughly equal amount of beads, or by making a homogeneous slurry of the resin in a suitable solvent or solvent mixture, and then adding the same volume of this slurry to each well. The reaction solvent, each different reactant, and the catalyst are then added to each individual well. The reaction plate is then stoppered and the desired reactions are then carried out, as described above. Reagents varying in their substituent groups occupy the well of each plate in a predetermined array, to achieve as ultimate products a unique benzofuran, or if preferred a predeterminated number of benzofurans, in each well. By using different combinations of substituents, a large number of different compounds with a common central benzofuran structure is obtained. For example, the synthesis may begin with four different compounds of formula (IIa), and each of these five may be reacted with different compounds of formula (III), such as 480 different compounds of formula (III), to provide 2,400 different benzofuran derivatives of formula (Ia). One more variation element, if desired, may be added during the cleavage of the compounds of formula (Ia) from the resin, as described above. For instance, by using a water/ethanol mixture, the free acid and its ethyl ester are formed in roughly equimolar amounts. For instance, by cleaving a discrete number of unique benzofurans a mixture of new different benzofuran set may be generated, each well containing a mixture of different structures, each mixture distinguisheable by the substituents $R_2$, $R_3$, $R_4$, $R_5$, but not by the substituent $R_1$, so that each well will contain the full mixture range. More variations introduced during the cleavage would lead to an ever-increasing number of compounds.

Alternatively, the process of the present invention can be carried out analogously to the "pin method" developed by Geysen et al. for combinatorial solid-phase peptide synthesis. A description of this method is offered for instance by Thompson and Ellman, *Chem. Rew.* (1996), 555–600. According to this method, a series of 96 pins are mounted on a block in an arrangement and spacing which correspond to a 96-well Microtiter reaction plate, and the surface of each pin is derivatised to contain terminal hydroxy or amino groups. The pin block is then lowered over a series of reaction plates in sequence to immerse the pins in the wells of the plates where coupling occurs. The various reactions are then performed as discussed above. These pins are commercially available as well as the pin blocks.

The following working examples are given to better illustrate the present invention, without being a limitation of the scope of the invention itself.

GENERAL PROCEDURE (1) Preparation of a compound of formula (II) wherein L=iodine, X=acetyl, $R_1$=$R_5$=H, A=CH, n=0 (4-acetoxy-3-iodobenzoic acid).

A 4% acqueous solution of sodium ipochlorite (34.5 g) is added dropwise to a stirred mixture of 4-hydroxybenzoic acid methyl ester (2.8 g, 19 mmoles), potassium iodide (3.1 g, 19 mmoles) and sodium methylate (1.0 g, 19 mmoles) in methyl alcohol (50 ml) at 0–3° C. The resulting mixture is stirred for 1 hour and treated with a 10% acqueous solution of sodium thiosulfate (20 ml). After acidification, 4-acetoxy-3-iodobenzoic acid methyl ester separates from the reaction mixture as a white powder (2.9 g). 4-Acetoxy-3-iodobenzoic acid methyl ester is hydrolyzed with 2N acqueous sodium hydroxide. The resulting 4-acetoxy-3-iodobenzoic acid (2.7 g, 10 mmoles) in 1N acqueous sodium hydroxide (25 ml) at 0° C. is treated with acetic anhydride (2.4 ml, 25 mmoles) in diethyl ether (15 ml). After work-up the title 4-acetoxy-3-iodobenzoic acid is obtained (2.8 g) as a white solid (m.p. 173–174° C., after cristallization from toluene).

(2) Coupling of the compound of formula (II) to the solid support.

Method A

The compound of formula (II) (0.4 g) is introduced into a 100 mL peptide reaction flask, along with tetrahydrofuran (THF) (50 mL), and a hydroxy resin (Tentagel™ hydroxy resin) (1.00 g) with a capacity of about 0.3–0.4 meq/g. To this mixture, an excess of $Ph_3P$ (triphenylphosphine) and DEAD (diethylazodicarboxylate), or optionally 10 mL of a mixture of $Ph_3P$ and DEAD in THF, are added. The mixture is vigorously shaken for 4 hours, then the solvents and excess reactants are filtered off. The resin is washed 5 times with THF, then with methanol (MeOH), and then with diethylether ($EtO_2$). The coupling cycle is optionally repeated twice, and then the resulting resin supporting the compound of formula (II) is dried in vacuum for 12 hours.

Method B

A Fmoc (fluorenylmethyloxycarbonyl) protected amino resin (100 mg), having a capacity of about 0.2 meq/g, is introduced in a 10 mL peptide reaction flask. Dimethylformamide (DMF) (3 mL) and piperidine (1 mL) are added, and the resulting mixture is vigorously shaken for 1 hour, then the solvents and excess reactant are filtered off. The resin is washed 5 times with a DMF/MeOH mixture, and then dried in vacuum for 12 hours. The resulting resin is suspended in DMF (4 mL), then OHBT (hydroxybenzotriazole) (56 mg), DCC (dicyclohexylcarbodiimide) (66 mg), and the compound of formula (II) (155 mg) are added. The mixture is vigorously shaken at room temperature overnight, then the solvents and excess reactants are filtered off. The resin is washed 5 times with DMF, MeOH, and then $CH_2Cl_2$. The coupling cycle is optionally repeated twice, and then the resulting resin supporting the compound of formula (II) is dried in vacuum for 12 hours.

(3) Deprotection of the hydroxyl group to obtain the compound of formula (Ia).

The above obtained dry resin (1.0 g), supporting the 3-iodo-4-acetoxybenzoic derivative of formula (II) as prepared above, is introduced into a round bottom flask, along with 60 ml of tetrahydrofuran, 20 ml of methanol, and 20 ml of 30% ammonia acqueous solution. The reaction mixture is kept at 20° C. with occasional shaking for 16 hours. Then the solvent is filtered off, the resin is washed 5 times with THF, MeOH, and diethylether, and the resulting solid support is dried in vacuum for 12 hours.

(4) Synthesis of the benzofuran derivatives on the solid support.

The above obtained dry resin (80 mg) supporting the 3-iodo-4-hydroxybenzoic derivative of formula (IIa) in an amount of 0.2 mmol/g resin, is introduced into a round bottom flask. A compound of formula (III) is added in an amount of 50 molar equivalents with respect to the molar amount of the supported compound of formula (IIa), then DMF (4.5 mL), and tetramethyl guanidine (0.5 mL) are added. $PdCl_2(PPh_3)_2$ (10 mg), and optionally CuI (8.0 mg), are added in sequence. The reaction flask is then stoppered and the reaction mixture is heated at 50–60° C. for 16 hours, with occasional stirring. The solvent and excess reactant are then removed by filtration, and the remaining brown-yellow solid support is rinsed five times in 2 mL of DMF, MeOH, and then $Et_2O$, each washing continuing for approximately 30 sec, with filtration between successive washings. To the solid support are then added 1.3 mL of i-PrOH and 3.3 mL of a 1N NaOH acqueous solution. The resulting mixture is heated at 40–50° C. for 8 hours, with occasional shaking, and then left at room temperature overnight. The mixture is then filtered to remove the solid support. The solid support is then rinsed three times with 3 mL of a i-PrOH/water mixture. The solution is evaporated, and the residual water solution is acidified with diluted HCl. Extaction with ethyl acetate (EtOAc) and concentration of the combined exatcts then provides the benzofuran derivatives of formula (Ia).

The final basic cleavage may be performed using MeOH/water or EtOH/water mixtures, so affording the corresponding esters of formula (I).

Following the above described general procedure, the following benzofuran derivatives were prepared:

2-(n-hexyl)-benzofuran-5-carboxylic acid

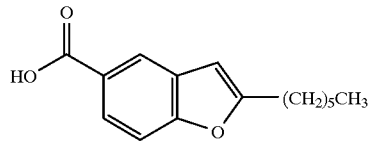

$^1$H NMR (200 MHz, DMSO-$d_6$) δ (ppm): 12.77 (1H, bs); 9.14 (1H, d); 7.81 (1H, dd); 7.55 (1H, d); 6.69 (1H, d); 2.77 (2H, t,); 1.67 (2H, m); 1.20–1.35 (6H, m); 0.84 (3H, m).

2-(3-Cl-propyl)-benzofuran-5-carboxylic acid

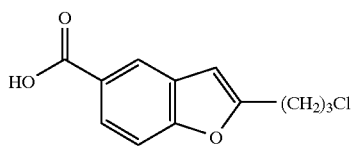

$^1$H NMR (200 MHz, CDCl$_3$) δ (ppm): 8.31 (1H, d); 8.03 (1H, dd); 7.46 (1H, d); 6.53 (1H, d); 3.62 (2H, t); 2.99 (2H, t); 2.24 (2H, m).
MS (FAB) m/z 239 [M+H]$^+$.

2-(3-Cl-propyl)-benzofuran-5-carboxylic acid, methyl ester

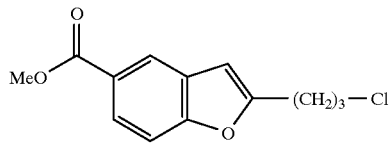

$^1$H NMR (200 MHz, CDCl$_3$) δ (ppm): 8.22 (1H, d) ; 7.96 (1H, dd); 7.43 (1H, d); 6.51 (1H, d); 3.93 (3H, s); 3.61 (2H, t); 2.98 (2H, t) ; 2.26 (2H, m).

2-(1-hydroxyethyl)-benzofuran-5-carboxylic acid

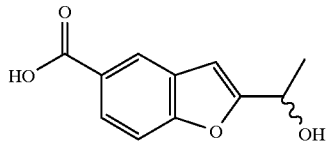

$^1$H NMR (200 MHz, DMSO-$d_6$) δ (ppm): 12.8 (1H, bs); 8.20 (1H, dd); 7.85 (1H, dd); 7.59 (1H, dd); 6.81 (1H, dd); 5.55 (1H, bs); 4.83 (1H, q) ; 1.45 (3H, d).
MS (EI) m/z 206 (M$^+$, 27); 191 [(M—CH$_3$)$^+$, 100].

2-(1-hydroxyethyl)-benzofuran-5-carboxylic acid, methyl ester

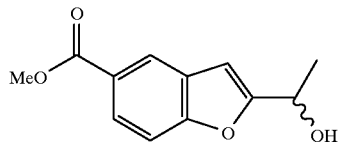

$^1$H NMR (200 MHz, CDCl$_3$) δ (ppm): 8.26 (1H, d); 7.98 (1H, dd); 7.46 (1H, dd); 6.64 (1H, s); 5.02 (1H, q); 3.93 (3H, s); 2.25 (1H, bs); 1.64 (3H, d).
MS (EI) m/z 220 (M$^+$, 31); 205 [(M—CH$_3$)$^+$, 100]; 189 [(M—OCH$_3$)$^+$, 15].

2-(N,N-diethylaminomethyl)-benzofuran-5-carboxylic acid, methyl ester

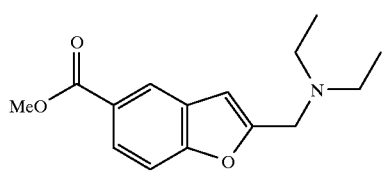

$^1$H NMR (200 MHz, CDCl$_3$) δ (ppm): 8.24 (1H, dd); 7.96 (1H, dd); 7.47 (1H, dt); 6.62 (1H, d); 3.93 (3H, s); 3.79 (2H, s); 2.61 (4H, q); 1.10 (6H, t).

2-t-butyl-benzofuran-5-carboxylic acid, methyl ester

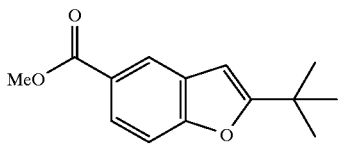

$^1$H NMR (200 MHz, CDCl$_3$) δ (ppm): 8.21 (1H, d); 7.94 (1H, dd); 7.42 (1H, d) ; 6.40 (1H, d) ; 3.93 (3H, s); 1.38 (9H, s).
MS (EI) m/z 232 (M$^+$, 24); 217 [(M—CH$_3$)$^+$, 100]; 201 [(M—OCH$_3$)+, 7].

2 -phenyl-benzofuran-5-carboxylic acid

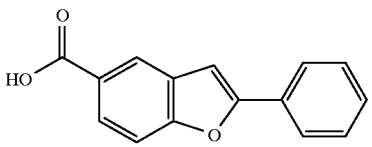

$^1$H NMR (200 MHz, DMSO-d$_6$) δ (ppm): 12.08 (1H, bs); 8.22 (1H, dd); 7.85–7.92 (3H, m); 7.67 (1H, ddd); 7.3–7.5 (4H, m).

2-phenyl-benzofuran-5-carboxylic acid, methyl ester

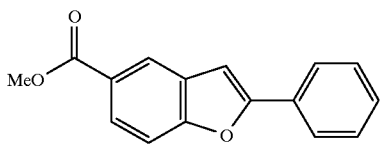

$^1$H NMR (CDCl$_3$) δ (ppm): 8.32 (1H, dd); 8.02 (1H, dd); 7.46 (1H, m); 7.4–7.9 (5H, m); 708 (1H, d); 3.95 (3H, s).
MS (EI) m/z 252 (M$^+$, 100); 221 [(M—OCH$_3$)$^+$, 91]; 193[(M—COOCH$_3$)$^+$, 47].

2-[N-t-butyloxycarbonyl (aminomethyl)]-benzofuran-5-carboxylic acid, methyl ester

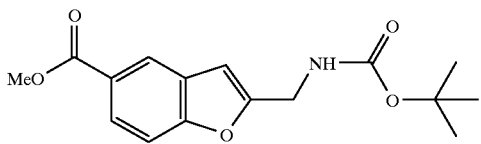

$^1$H NMR (200 MHz, CDCl$_3$) δ (ppm): 8.25 (1H, d); 7.98 (1H, dd); 7.45 (1H, dd); 6.65 (1H, d); 5.0 (1H, bs); 4.45 (2H, d,); 3.93 (3H, S); 1.46 (9H, s).

(4) Synthesis of a library of benzofuran derivatives.

The above prepared dry resin (1.2 g), supporting the substituted 3-iodo-4-hydroxybenzoic derivative of formula (IIa) in an amount of 0.2 mmol/g resin, is divided into 96 portions having roughly the same weight, and each portion is added to a well of a Microtiter 96-well polypropylene plate. A compound of formula (III) is added in inert atmosphere in an amount of 50 mole equivalents with respect to the molar amount of the supported compound of formula (IIa). Then a solution of DMF (0.75 mL) and tetramethyl guanidine (0.05 mL), containing PdCl$_2$ (PPh$_3$)$_2$ (1.8 mg), and optionally CuI (1.1 mg), are added in inert atmosphere. Each well is then stoppered and the reaction plate is heated at 50–60° C. for 16 hours in an oven, with occasional shaking. The solvent and excess reactant is then removed by filtration from each well, and the remaining brown-yellow solid support is rinsed five times in 1 mL of DMF, and then 1 mL of MeOH, each washing lasting approximately 30 sec, with filtration between successive washings. To the solid support in each well are then added 0.2 mL of i-PrOH and 0.5 mL of 2N NaOH acqueous solution. The resulting mixture is heated at 40–50° C. for nine hours, with occasional shaking, and then left at room temperature overnight. Each well is then filtered to remove the solid support. The solid support is then rinsed three times with 0.5 mL of an i-PrOH/water mixture. The solution is evaporated by using, e.g., an oven or other commercial equipment, such as a Microtiter plate speed vacuum apparatus, then the pH of the residual water solution is adjusted to about 7 with 2N HCl. Concentration as above then provides the products of formula (I) in the dry form.

Alternatively, the final alkaline cleavage may be performed by using MeOH/water or EtOH/water mixtures, so affording the corresponding esters of formula (I).

An array of 60 molecules around the following benzofuran structural theme was generated according to the above described method.

| Organic Residue | R$_8$ | Organic Residue | R$_8$ |
|---|---|---|---|
| (CH$_2$)$_2$CH$_3$ | H | CH$_2$-S-phenyl | H |
| CH$_2$CH(CH$_3$)CH$_2$CH$_3$ | H | CH$_2$OH | H |
| (CH$_2$)$_2$CH(CH$_3$)$_2$ | H | CH(OH)CH$_3$ | H |
| C(CH$_3$)$_3$ | H | C(OH)(CH$_3$)$_2$ | H |
| CH$_2$cyclohexyl | H | (CH$_2$)$_4$OH | H |
| cyclopentyl | H | CH$_2$CH(OH)CH$_3$ | H |
| CH$_2$Ph | H | CH$_2$CH(OH)CH$_2$CH$_3$ | H |
| (CH$_2$)$_3$Ph | H | CH$_2$NH$_2$ | H |
| Ph | H | CH$_2$NHCH$_3$ | H |
| p-CH$_3$—Ph | H | CH$_2$N(CH$_3$)$_2$ | H |
| p-(CH$_3$)$_2$CHCH$_2$—Ph | H | CH$_2$N(C$_2$H$_5$)$_2$ | H |
| m-NH$_2$—Ph | H | (CH$_2$)$_3$CN | H |
| p-CH$_3$O—Ph | H | (CH$_2$)$_3$Cl | H |
| p-F—Ph | H | biphenyl | H |
| p-Cl—Ph | H | m-OH—Ph | H |
| (CH$_2$)$_2$CH$_3$ | Me | CH$_2$—S-phenyl | Me |
| CH$_2$CH(CH$_3$)CH$_2$CH$_3$ | Me | CH$_2$OH | Me |
| (CH$_2$)$_2$CH(CH$_3$)$_2$ | Me | CH(OH)CH$_3$ | Me |
| C(CH$_3$)$_3$ | Me | C(OH)(CH$_3$)$_2$ | Me |
| CH$_2$cyclohexyl | Me | (CH$_2$)$_4$OH | Me |
| cyclopentyl | Me | CH$_2$CH(OH)CH$_3$ | Me |
| CH$_2$Ph | Me | CH$_2$CH(OH)CH$_2$CH$_3$ | Me |
| (CH$_2$)$_3$Ph | Me | CH$_2$NH$_2$ | Me |
| Ph | Me | CH$_2$NHCH$_3$ | Me |
| p-CH$_3$—Ph | Me | CH$_2$N(CH$_3$)2 | Me |
| p-(CH$_3$)$_2$CHCH$_2$—Ph | Me | CH$_2$N(C$_2$H$_5$)$_2$ | Me |
| m-NH$_2$—Ph | Me | (CH$_2$)$_3$CN | Me |
| p-CH$_3$O—Ph | Me | (CH$_2$)$_3$Cl | Me |
| p-F—Ph | Me | byphenyl | Me |
| p-Cl—Ph | Me | m-OH—Ph | Me |

(5) Screening.

After evaporation of the solvents, as described above, the screening may be performed by any of the standard methods for performing screens on Microtiter plates. For instance, the methods described by Geysen et al. in *J. Immunobiological Methods* (1987) 102: 259–274, can be employed, if the case suitably modified to fit the tested compounds.

We claim:
1. A process for producing a plurality of benzofuran derivatives of formula:

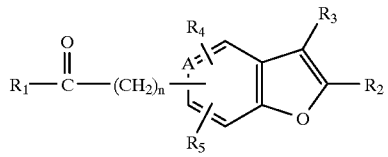

(I)

wherein:

$R_2$, $R_3$, $R_4$, and $R_5$, which are the same or different, are each hydrogen or a structural diversity element, with the proviso that at least one of $R_2$, $R_3$, $R_4$, and $R_5$ is different from hydrogen;

$R_1$ is —$NR_6R_7$ or —$OR_8$, wherein $R_6$, $R_7$, and $R_8$, which are the same or different, are each hydrogen or a structural diversity element;

A is CH or N, and may occupy any of the unsubstituted positions of the phenyl ring; and n is zero or an integer from 1 to 4;

which process comprises the steps of:

(a) coupling to a solid support a first scaffold of formula:

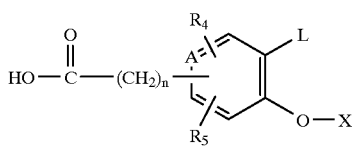

(II)

wherein:

$R_4$ and $R_5$, which are the same or different, are each hydrogen or a structural diversity element;

A is CH or N, and may occupy any of the unsubstituted positions of the phenyl ring;

n is zero or an integer from 1 to 4;

L is a leaving group; and

X is a hydroxy protecting group;

(b) deprotecting the hydroxyl group of the scaffold of formula (II) coupled to the solid support, to obtain a deprotected first scaffold of formula:

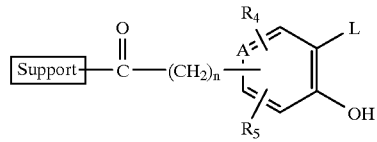

(IIa)

(c) reacting said deprotected first scaffold of formula (IIa) coupled to the solid support with a second scaffold of formula:

(III)

wherein $R_2$ and $R_3$, which are the same or different, are, each hydrogen or a structural diversity element;

in the presence of a Pd(0) complex or a Pd(II) salt as catalyst, and optionally in the presence of a Cu(I) salt, to give benzofuran derivatives of formula (Ia) supported on the solid support:

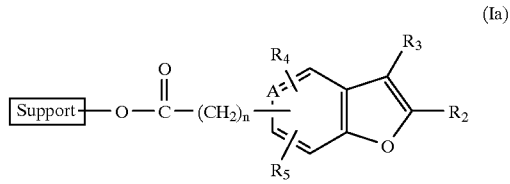

(Ia)

(d) optionally cleaving the said derivatives of formula (Ia) from the solid support to give the benzofuran derivatives of formula (I).

2. A process according to claim 1, wherein in formula (II) the leaving group L is a halogen atom or a group —$OSO_2R_9$ in which $R_9$ is $C_1$–$C_6$ alkyl, $C_6$–$C_{10}$ aryl, $C_7$–$C_{12}$ arylalkyl or alkylaryl, optionally substituted by one or more fluorine atoms.

3. A process according to claim 1, wherein in formula (II) the hydroxy protecting group X is an acyl group or a trisubstituted silyl group.

4. A process according to claim 1, wherein step (c) is carried out in an organic solvent, in the presence of a base in excess.

* * * * *